United States Patent
Assing et al.

(10) Patent No.: US 9,936,725 B2
(45) Date of Patent: Apr. 10, 2018

(54) METHOD, METERING DEVICE AND METERING VALVE FOR THE ASEPTIC MEASURED DELIVERY OF A LIQUID ADDITIVE INTO A FORCED FLOW OF A BASE PRODUCT

(71) Applicant: GEA TDS GmbH, Sarstedt (DE)

(72) Inventors: Hubert Assing, Ahaus (DE); Andreas Schmied, Dülmen (DE); Uwe Schwenzow, Ahaus (DE); Helmut Buss, Heiden (DE); Franz Tasler, Coesfeld (DE)

(73) Assignee: GEA TDS GmbH, Sarstedt (DE)

( * ) Notice: Subject to any disclaimer, the term of this patent is extended or adjusted under 35 U.S.C. 154(b) by 22 days.

(21) Appl. No.: 15/274,349

(22) Filed: Sep. 23, 2016

(65) Prior Publication Data

US 2017/0006903 A1    Jan. 12, 2017

Related U.S. Application Data (62) Division of application No. 14/383,437, filed as application No. PCT/EP2012/001020 on Mar. 8, 2012, now Pat. No. 9,491,964.

(51) Int. Cl.
*A61L 2/00* (2006.01)
*F16L 37/06* (2006.01)
(Continued)

(52) U.S. Cl.
CPC ............... *A23L 3/001* (2013.01); *A23L 3/22* (2013.01); *A61L 2/07* (2013.01); *G01F 11/32* (2013.01); *A23V 2002/00* (2013.01)

(58) Field of Classification Search
CPC .... A61L 2/00; A61L 2/07; A61L 2/18; A61M 1/168; G01N 35/10
(Continued)

(56) References Cited

U.S. PATENT DOCUMENTS

| 2002/0172745 A1 | 11/2002 | Palaniappan |
| 2005/0031751 A1 | 2/2005 | Weng et al. |
| 2008/0100061 A1* | 5/2008 | Sage .................. A61B 5/6864 285/305 |

FOREIGN PATENT DOCUMENTS

| DE | 10337057 A1 | 3/2005 |
| DE | 10 2007 056 833 A1 | 5/2009 |
| EP | 0447760 A1 | 9/1991 |

OTHER PUBLICATIONS

Mario Jekle: (German Document) Lactosefreie und—reduzierte Milchprodukte; Nov. 18, 2004.
(Continued)

*Primary Examiner* — Monzer R Chorbaji
(74) *Attorney, Agent, or Firm* — Vidas, Arrett & Steinkraus, P.A.

(57) ABSTRACT

A metering device with a product conduit section, through which a base product forcibly flows, with at least one storage container for an additive, which is connected with an associated metering point respectively via a removal conduit, which is arranged on or respectively in the product conduit section, with a mechanism for forcibly conveying the additive, with quantity-based capturing of the base product and of the additive, with sterile steam and with a control device assigned to the metering device. The metering point is provided within a metering valve, which forms a product chamber, into which the product conduit section opens and from which it exits, an initial chamber and a partial chamber as well as a receiver of an end section and of a terminal side.

13 Claims, 6 Drawing Sheets

(51) Int. Cl.
*A23L 3/00* (2006.01)
*A23L 3/22* (2006.01)
*A61L 2/07* (2006.01)
*G01F 11/32* (2006.01)

(58) Field of Classification Search
USPC ....... 422/1, 26, 28, 292; 134/22.15; 285/305
See application file for complete search history.

(56) References Cited

OTHER PUBLICATIONS

Alfred Töpel: (German Document) Chemie u. Physik der Milch Behr's Verlag DE, 2004.
Author Unknown: (German Document) Tetra FlexDos.

* cited by examiner

METHOD, METERING DEVICE AND METERING VALVE FOR THE ASEPTIC MEASURED DELIVERY OF A LIQUID ADDITIVE INTO A FORCED FLOW OF A BASE PRODUCT

CROSS-REFERENCE TO RELATED APPLICATIONS

This application is a Continuation application from Ser. No. 14/383,437 which is a national stage application of PCT/EP2012/001020, filed on Mar. 8, 2012.

STATEMENT REGARDING FEDERALLY SPONSORED RESEARCH

Not applicable.

BACKGROUND OF THE INVENTION

The invention relates to a method for the aseptic measured delivery of a liquid additive, in particular an additive generated and stored under aseptic conditions, into a forced flow of a base product, which is in particular also provided under aseptic conditions, wherein the additive is removed from a storage container under aseptic conditions by means of a removal conduit and is fed via an end section of the removal conduit to the base product, which flows through a product chamber, as well as a metering device for performing the method and a metering valve for the metering device.

BRIEF SUMMARY OF THE INVENTION

Liquid aseptic additives of the aforementioned type, like enzymes, flavors, colorings, lipids, probiotic bacteria and other foodstuffs, are metered into a food functioning as an aseptic base product of the aforementioned type in order to provide them with special properties. Since these additives can be heat-sensitive, delivery of these additives into the base product takes place right before its filling and after its heat treatment for killing unwanted germs, for example an ultra-high-temperature treatment (UHT heat treatment), and preferably within the framework of a so-called inline dosing. The measuring delivery must take place under aseptic conditions and with a sterile additive also stored under aseptic conditions, so that the base product produced aseptically and thus germ-free during the course of the heat treatment is not infected with germs in the phase of the measured delivery.

A widespread use case, in which an enzyme is used as an additive, is the production of lactose-reduced or lactose-free products. Lactase is used here to enzymatically split the lactose. These products are consumed above all by people who suffer from a lack of β-galactosidase in the intestinal tract. Another field of application for lactose-reduced milk and related substances is the market for reduced-calorie products. During the lactose splitting, one molecule each of D-glucose and β-D-galactose is created [TÖPEL, 2004, pg. 99; [1] JEKLE; Lebensmitteltechnologisches Seminar, Lactosefreie und -reduzierte Milchprodukte, 2004 (Food Technology Seminar, Lactose-Free and -Reduced Milk Products)]. Each of these molecules is sweeter than lactose so that a considerably sweeter product with an unchanged nutritional value can be produced. In order to ensure an almost complete hydrolysis of the lactose, e.g. the enzyme β-galactosidase can be used in production. In order to be able to reduce the process costs of the hydrolysis, methods were developed whereby the enzyme is added immediately before the filling [1]. This has the advantage that the distribution phase can be used as hydrolysis time and lower enzyme doses are thus realizable. The measured delivery rate of the enzyme in question ranges between 0.2 to 4 ml enzyme/liter (200 to 4000 ppm).

In the publication by the company Tetra Pak Processing GmbH, Tetra FlexDos™, Flexibles aseptisches Dosiersystem für flüssiges Zusatzstoffe (Flexible Aseptic Dosing System for Liquid Additives), PD 10080 de 2007-02, a metering device is described, with which an aseptic inline dosing of this liquid additive into a base product is performed using a storage container designed in the form of a flexible bag, in which an additive of the type in question is stored. For this purpose, the ready-to-use 5- or 10-liter bag filled with the sterile additive under aseptic conditions, which is in turn received in a pail-like overwrap, is hung into the metering device. In the course of the metering, a separate hose arrangement functioning as a removal arrangement, which is connected to the bag before the metering via a special adapter, is used to transfer the additive from the bag into the base product. The hose arrangement and the bag are produced and provided separately from each other; as a rule, they originate from different manufacturers and are first brought together and permanently connected in the metering device. An injection needle is arranged on the end of the hose arrangement facing away from the adapter, via which the additive is delivered in a measured manner into the base product at an injection point by means of a peristaltic pump acting on the hose arrangement from the outside. The injection point is located on a tube socket of a tube, in which the base product flows. The injection point is thereby designed as a chamber, which then functions as a sterilizing steam barrier when suitable sterile steam flows through it. Two membranes connected in series, the first between the surrounding area and the inner space of the chamber, the second between the inner space of the chamber and the inner space of the tube, must be penetrated by the injection needle before the measured delivery can begin.

The known metering device with the used bag and the separate hose arrangement has disadvantages in particular in the area of the bag and the coupling of the hose arrangement and at the injection point and involves critical handling steps, which can call into question the absolutely required sterility of the measured delivery process.

The removal connection at the bag can be exposed to damaging environmental influences and/or possible faulty handling before the coupling of the hose arrangement, which can impair the sterility of the critical surfaces combined in the course of the coupling process and supplying the additive to be delivered in a measured manner. A sterilization of these critical surfaces is no longer possible after execution of the coupling process. Since the bag and the hose arrangement are located separately from each other in an overwrap, a relatively expensive and hardly user-friendly starting point as well as a more than theoretical possibility of the contamination of the critical surfaces with germs result solely from this storage and handling situation.

At the injection point, it must be relied upon that sufficient sterilization takes place during the insertion and penetration process of the injection needle. Thereby, neither the holding time of the injection needle in the steam barrier nor the temperature control at the moved injection needle is defined or conditioned. An interruption in the measured delivery is then problematic in terms of the condition of the internal loading of the injection needle with additive when it is temporarily removed from its measured delivery position due to a process interruption and, because the bag is still partially filled with high-quality additive that still needs to be used, is returned to its measured delivery position upon continuation of the measured delivery.

There are no methodical, reproducible or clearly conditioned conditions neither during the coupling of the hose arrangement or during the sterilization of the injection needle; accidental and systematic errors can occur and call into question the safety of the aseptic measured delivery.

The purpose of the present invention is to find a method of the generic type and to suggest a metering device for performing the method and a metering valve for the metering device, which avoid the disadvantages of the prior art and guarantee aseptic measured delivery that is characterized by methodical, reproducible and clearly conditioned and controlled conditions. The present invention has the special object of delivering in a measured manner the smallest aseptic quantities of an additive up to a maximum of 250 ppm directly into the forced flow of an aseptic base product.

SUMMARY OF THE INVENTION

The innovative fundamental idea consists in that a terminal part of the end section of the removal conduit, in whatever form it is designed, is at least sterilized under planned methodical, reproducible and clearly defined and controlled conditions before it temporarily arrives in its measured delivery position and readiness. The terminal part can be an integral part of the end section or a part designed separately from the end section, wherein in the last case this separate part can be designed with a controllable outlet opening, for example in the shape of a small metering valve. The terminal part of the end section is thereby still located outside of the product chamber, in which the measured delivery takes place, and areas of the terminal part of the end section, which lie in its later measured delivery position at the penetration point within a sealing means required there and, in relation to the product chamber, also on the side of the sealing means facing away from the product chamber, are included in the sterilization. Only after at least this sterilization, which preferably takes place in a temperature-monitored manner, does the terminal part of the end section arrive in its measured delivery position, wherein a connection to the product chamber has not yet been established and this position is called the standby position. In the standby position, the terminal part of the end section is sealed at its penetration point by means of the sealing means previously sterilized at least partially. A connection to the production chamber is now established under these clearly defined and controlled conditions and the aseptic measured delivery is started.

The procedural solution according to the invention is manifested through the following treatment steps for the end section, before the latter feeds the additive to the base product:

(a) the end section is temporarily introduced a certain distance into an initial chamber from one side or is permanently positioned therein and is sealed at the penetration point to this initial chamber, wherein the latter can optionally be opened towards the product chamber;

(b) a terminal part of the end section that projects into the initial chamber in a sealed manner is at least sterilized, wherein all regions of the initial chamber also being included in this treatment;

(c) the terminal part of the end section is slid a certain distance into a partial chamber that can optionally be sealably divided from the initial chamber, the terminal part being sealed at the end of the sliding action at the penetration point to the partial chamber by means of a sealing means treated as per treatment step (b);

(d) the partial chamber is opened towards the product chamber.

In order, for one, to shorten the period of time between sterilization and the start of the measured delivery and, on the other hand, to prevent a burning of the potentially temperature-sensitive additive in the sterilized area of the end section, it is expedient that a cooling under sterile conditions follows the sterilization according to treatment step (b).

The sterilization takes place in a generally known manner expediently with sterile steam and the cooling takes place expediently with sterile air, wherein, according to another suggestion, this temperature treatment is performed in a controlled manner in that the sterilization and the cooling respectively take place in a temperature-monitored manner. Only when a specified temperature threshold is reached at the temperature measurement point, which, seen in the flow direction of the respective fluid, is arranged downstream of the terminal part of the removal conduit to be treated, is the respective temperature treatment ended. The sterilization is thereby performed in a productive manner at a temperature above 125° C. and the cooling takes place to a temperature below 50° C.

In order to ensure that the additive does not arrive in the end section prematurely, it is ensured in the progression of the suggested method that the removal conduit remains free of the additive until the execution of the treatment step (b) or (c) and that the additive is first delivered up to the discharge point of the terminal part after this.

Since it cannot be excluded that during the pushing forward to the discharge point of the terminal part, the additive escapes there in more less small quantities and the measuring delivery can thereby be falsified at least initially, another suggestion provides that a flushing of the initial chamber with sterile condensate is optionally performed below a temperature of 50° C. This flushing can be performed according to the treatment step (b) or (c), wherein according to the treatment step (c) the initial chamber is to be established first before the flushing is initiated. In order to free the initial chamber from the sterile condensate remaining therein after the flushing, it is advantageous that it is blown out by means of sterile air subsequent to the flushing of the initial chamber.

It is ensured through metrological provisions that the additive is delivered in a measured manner in proportion to quantity to the flowing base product. The necessary accuracy of the measured delivery is achieved when the transport of the additive in the removal conduit and, if applicable, also the removal from the storage container takes place forced in a generally known manner.

The metering device for performing the method according to the invention assumes in the generally known manner a metering device with a product conduit section, through which the base product flows in a forced manner and which is equipped with at least one storage container for the additive, which is respectively connected with an associated metering position via the removal conduit. As a rule, two storage containers are provided, which are operated in alternation in order to thus ensure a continuous measured delivery. Furthermore, third means for the forced conveyance of the additive, first and second means for the quantity-based capturing of the base product and of the additive, fourth means for providing sterile steam and a control device assigned to the metering device are provided. The solution according to the invention is characterized in that the metering point assigned to the respective storage container is respectively provided within a metering valve, each of which on their own forms the product chamber, into which the product conduit section opens into and out of the latter, the initial chamber and the partial chamber as well as a receiver of the end section and of the terminal part.

An advantageous embodiment of the metering device provides that that part of the initial chamber, which remains after division of the partial chamber, has an infeed and a discharge channel, which are optionally respectively blockable via an associated stop valve and wherein the infeed channel can be connected at least with the fourth means for providing sterile steam. A further treatment of the initial chamber within the framework of a flushing, cooling or a blowing out is possible in a simple manner in that the infeed channel is optionally connectable with a fifth means for providing a sterile condensate and/or a sixth means for providing sterile air.

An examination to determine whether sterilization or cooling takes places above or below a sufficient temperature is expediently and simply ensured in that a temperature sensor is arranged in the discharge channel or downstream directly subsequent to the discharge channel.

Higher aseptic security compared to the known state of the art is achieved in that the storage container and at least the removal conduit form a sterile unit in the delivery state. A preferred embodiment of the storage container provides that it is made of a flexible bag made of semi-transparent ethylene-vinyl acetate (EVA). Before the filling of the bag with the additive, the removal conduit is permanently sealed with the bag. This connection can preferably be realized in a form- and/or force-fitting manner, for example in the form of an elastically ductile coupling so that a joining of the bag with the removal conduit to a permanently sealed unit is given in the simplest manner. But the connection can also be executed as a surface-connection, for example through welding. In each case, the unit, consisting of the bag filled with the additive and the removal conduit preferably fixed on it, in connection with the integrated injection needle, the fixed tube with smooth end or the adapter, can be tightly sealed in a PE overwrap and subjected to a suitable treatment, for example through a sterilizing irradiation, preferably a gamma irradiation, overall for the purpose of external sterilization. This solution according to the invention safely eliminates the otherwise existing possibility of impairment of the sterilization of the connection when the latter is established only after the filling of the bag with the additive and before the measured delivery of the aseptic additive to the aseptic base product.

In order to also establish permanently sterile conditions in the area of the connection of the bag to the removal conduit after the filling of the bag with the additive, another embodiment provides that a pressure-control valve is arranged in this connection, with which a fluid-accessible connection is established between the inner space of the bag and the removal conduit through irreversible breaking of a barrier at a predetermined breaking point. The connection with the removal conduit is only established shortly before the start of the measured delivery so that the removal conduit remains completely free of additive up until this point.

So that this type of arrangement can be used not only in the metering devices according to the invention but also in known ones, it is productive that the end section of the removal conduit with its integral terminal part is designed as one piece as an injection needle. In other cases, in which the removal conduit does not open into the measured delivery position via an injection needle but is rather connected within the metering valve according to the invention according to the proportion of the suggested measured delivery method, the end section with its integral terminal part can also be designed as one piece as a tube with a smooth end, which is permanent or deformable in a ductile manner.

But the measured delivery method and the metering device for performing the method also enable the use of an end section, in which the terminal part is designed separately from the end section and with a controllable discharge opening, for example in the form of a small metering valve. In this case, the end section can in turn be designed as an injection needle or tube with a smooth end, which is permanent or deformable in a ductile manner, or as an adapter for producing a fluid-accessible connection with the terminal part, wherein the end section is then connected with the terminal part in a fluid-accessible manner.

A metering valve according to the invention for the metering device is characterized among other things by the following components:

- a first and a second sealing device for the terminal part of the removal conduit;
- a first sleeve, which receives the terminal part of the removal conduit and the removal conduit and which is driven in an axially displaceable manner by a spring piston drive with a second lifting movement;
- a clamping and pressing device, which is moved in an axially displaceable manner with the spring piston drive, fixes the removal conduit axially and radially and ensures the pressing force in the first sealing device for generating sufficient sealing effect in a first sealing means at the penetration point of the terminal part to the initial chamber.

In addition to these components, the metering valve has the following characteristics:

- a valve housing arranged in the product conduit section and surrounding the product chamber;
- a housing closing body closing the valve housing on one side with a passage opening to the product chamber;
- a spool, which engages in the valve housing from the side of the valve housing facing away from the passage opening and, after a first lifting movement in its one end position, the closed position, in the circumferential area of the passage opening, which is designed as the first seating, is in abutment with a spool seating,
- a chamber-forming spool recess provided in the front surface of the spool facing the passage opening, which forms the initial chamber together with a chamber located in the housing closure body between the passage opening and the front-side, displaceable end of the first sleeve, wherein the chamber located in the housing closure body is connected with the surrounding area of the metering valve via an infeed and a discharge channel;
- a closure piston, which is penetrated by the terminal part of the end section and is arranged on a bearing journal arranged on the end side on the first sleeve and protruding into the initial chamber.

Within the framework of the invention, the closure piston is particularly important due to its end positions, a closed and an open position, determined by the second lifting movement, in view of the second sealing device provided in it and acting on a second sealing means:

the closure piston is in sealing abutment in its end position, the closed position, generated by a drive spring in the spring piston drive after the second lifting movement, in the circumferential area of the passage opening, which is designed as the second seating, wherein the closure piston in its closed position between itself and the spool recess divides the partial chamber from the initial chamber and the closure piston is sealed off with respect to the terminal part by the axially and radially pressed second sealing means;

in another end position of the closure piston, the open position, generated with the second lifting movement, the second sealing means is released from the terminal part by a gap's width and all surfaces and areas of the initial chamber are accessible for application of a fluid, the sterile steam, the sterile condensate or the sterile air.

The construction of the metering valve is simplified when the end section of the housing closure body facing away from the valve housing is designed as a drive piston of the spring piston drive and is penetrated shiftably and sealed by the first sleeve, an assigned drive housing is designed in a pot-like manner and penetrated by the first sleeve and is connected with it in a form- and force-fitting manner, and when the drive spring on one side on the drive piston and on the other side on the first sleeve, preferably on a valve spring retainer designed on it, in a manner such that the reset force of the drive spring transfers the closure piston into its closed position.

Another embodiment provides that the drive housing on its side facing away from the drive piston transitions into a pot-like clamping housing of the clamping and pressing device restricted by a cap nut and that the cap nut acts via conical effective areas on a collet penetrated by the end section such that the end section is determined axially and radially by the collet.

A sufficient and permanent sealing of the first sealing means with respect to the terminal part is thereby ensured in that the collet is connected with the one end of a second sleeve received in the first sleeve and completely penetrated by the end section and acts axially on the latter such that it presses the first sealing means axially and radially with its other end.

A sufficient and permanent sealing of the second sealing means arranged in the closure piston with respect to the terminal part is ensured in that the closure piston and the bearing journal engaging in it form a wedge-shaped annular space surrounding the terminal part, which tapers from inside to outside and receives the second sealing means. In the closed position of the closure piston, the flanks of the wedge-shaped annular space converge far enough that the second sealing means is pressed axially and radially and is thus sealed against the terminal part. In the open position of the closure piston, the flanks of the wedge-shaped annular space are spaced apart from each other far enough that the second sealing means broadens and is spaced apart from the terminal part by a gap's width.

BRIEF DESCRIPTION OF THE SEVERAL VIEWS OF THE DRAWINGS

A more detailed representation of the invention results from the following description and the included figures of the drawing as well as from the claims. While the invention is realized in a variety of designs of a method, a metering device and a metering valve, the drawing describes a method, a metering device and a metering valve respectively in a preferred embodiment. They show:

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated A metering device 10 for performing the method according to the invention (FIG. 1) is provided as a rule at least in duplicate, wherein a first metering device 10.1 and a second metering device 10.2 for guaranteeing a continuous measured delivery process, which must be maintained over a longer production period, are arranged next to each other in a production line section 12, through which an aseptic base product P forcibly flows and leads for example to a filling machine 16. A storage container 18 for an aseptic, liquid additive Z is assigned to the metering device 10, which is connected with a metering point I arranged on or respectively in the product conduit section 12 via a removal conduit 18a. In the case of two metering devices 10.1, 10.2, which are operated in alternation, a first storage container 18.1 and a first metering point I.1 are assigned to the first metering device 10.1 and a second storage container 18.2 and a second metering point I.2 are assigned to the second metering device 10.2. The below description is limited to the general structure of a metering device 10, and components that may necessarily exist in duplicate are no longer differentiated in the case of two metering devices 10.1, 10.2 arranged next to each other.

In the removal conduit 18a, a third means 22 is provided for forced conveyance of the additive Z to the metering point I, for example a rotating displacement pump, preferably a peristaltic pump. In the case of a peristaltic pump, the conveying mechanism acts from outside on the removal conduit 18a designed in the form of a ductilely deformable hose in a manner such that there is no direct contact between the conveying mechanism and the additive Z.

Another option for forcibly conveying the additive Z to the metering point I is for example to place the additive Z in the storage container 18 under excess pressure in relation to the pressure at the discharge point of the removal conduit 18a at the metering point I. This can hereby be pressurization of the storage container 18 from inside, for example with sterile air, or also mechanical, hydraulic or pneumatic pressurization from outside when the storage container 18 is designed in the form of a ductilely deformable bag. In the case of the initially named option of the forced conveyance for example through a peristaltic pump, the removal conduit 18*a* is designed open at the discharge point of a terminal part E1 of its end section E (for this, see FIG. 2) and namely in the form e.g. of an injection needle 18*b* or of a hard or ductilely deformable tube with smooth end 18*c*. The terminal part E1 is hereby an integral part of the end section E. In the case of the secondly named option of the forced conveyance for example through pressurization of the storage container 18, the terminal part E1 is designed separately from the end section E and with a controllable discharge opening, wherein the end section E in turn can be designed as an injection needle 18*b* or hard or ductilely deformable tube with smooth end 18*c* or as an adapter 18*d* for establishing a fluid-accessible connection with the terminal part E1 and the end section E is connected with the terminal part E1 in a fluid-accessible manner and under aseptic conditions. In this embodiment, the terminal part E1 can be a small, controllable metering valve, which is permanently positioned at the metering point I and is optionally connected temporarily with the aforementioned different designs 18*b*, 18*c* or 18*d* of the end section E.

The metering device 10 is equipped with a first means 14, for example a quantity flow meter, arranged upstream of the metering point I in the product conduit section 12, for capturing the quantity of the base product P flowing there. Furthermore, a second means 20 is provided, with which the quantity of the additive Z flowing to the metering point I is captured. In the case of the second means 20, a preferred embodiment includes for example a high-precision scale, on which the storage container 18 is hung via a suspension 20*a*. The third means 22, the preferably used peristaltic pump, is connection with a speed regulation device 36. The first and second means 14, 20 as well as the third means 22 in connection with the speed regulation device 36 are respectively connected with a control device 50 via signal lines 40, 42 and 44 so that the additive Z can be delivered to the flowing base project P in a measured manner flow-proportional to the quantity.

The metering device 10 also has a fourth means 24 for providing sterile steam D for the sterilization, the temperature of which can be adjusted in the generally known manner to the sterilization conditions. If the sterile steam D is fed via the fifth means 24*a*, for example a heat exchanger supplied with soft water W, then sterile condensate K for the flushing within the framework of the method according to the invention can then be provided by this arrangement. Moreover, a sixth means 24*b* for providing sterile air L is provided, with which the cooling and blowing out can be executed within the framework of the method according to the invention. Sterile steam D and sterile condensate K are supplied via a first line 24*c* switchable by means of a third stop valve 30 and the sterile air L is supplied to a third line 24*e* via a second line 24*d* switchable by means of a fourth stop valve 32. The latter is switchable via a first stop valve 26 and connected to a metering valve 100. It continues behind the metering valve 100, seen in the flow direction of the respective fluid F, which can be steam D, sterile condensate K or sterile air L, can be switched there via a second stop valve 28 and opens into a drain 34. The temperature of the fluid F flowing downstream from the metering valve 100 in the third line 24*e* can be measured above a temperature sensor 38, which is connected with the control device 50 via a fourth signal line 46. The signals received by the control device 50 are processes there according to the method according to the invention and control signals for the metering valve 100 are generated from this, which are supplied to the latter via a control line 48.

Figure 1:
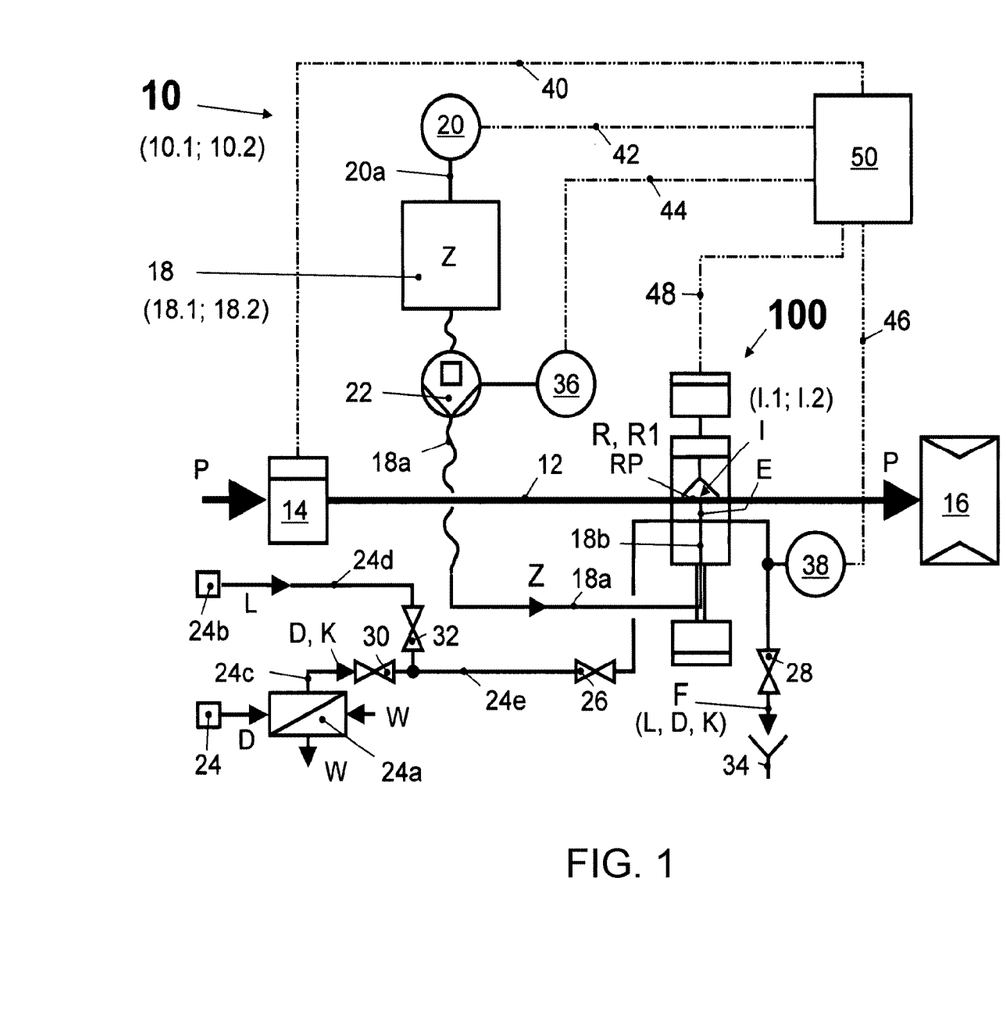
FIG. 1 in a very simplified schematic representation, a metering device for performing the method according to the invention, wherein only a single metering device is shown, while as a rule at least two metering devices are operated in alternation.
Figure 2:
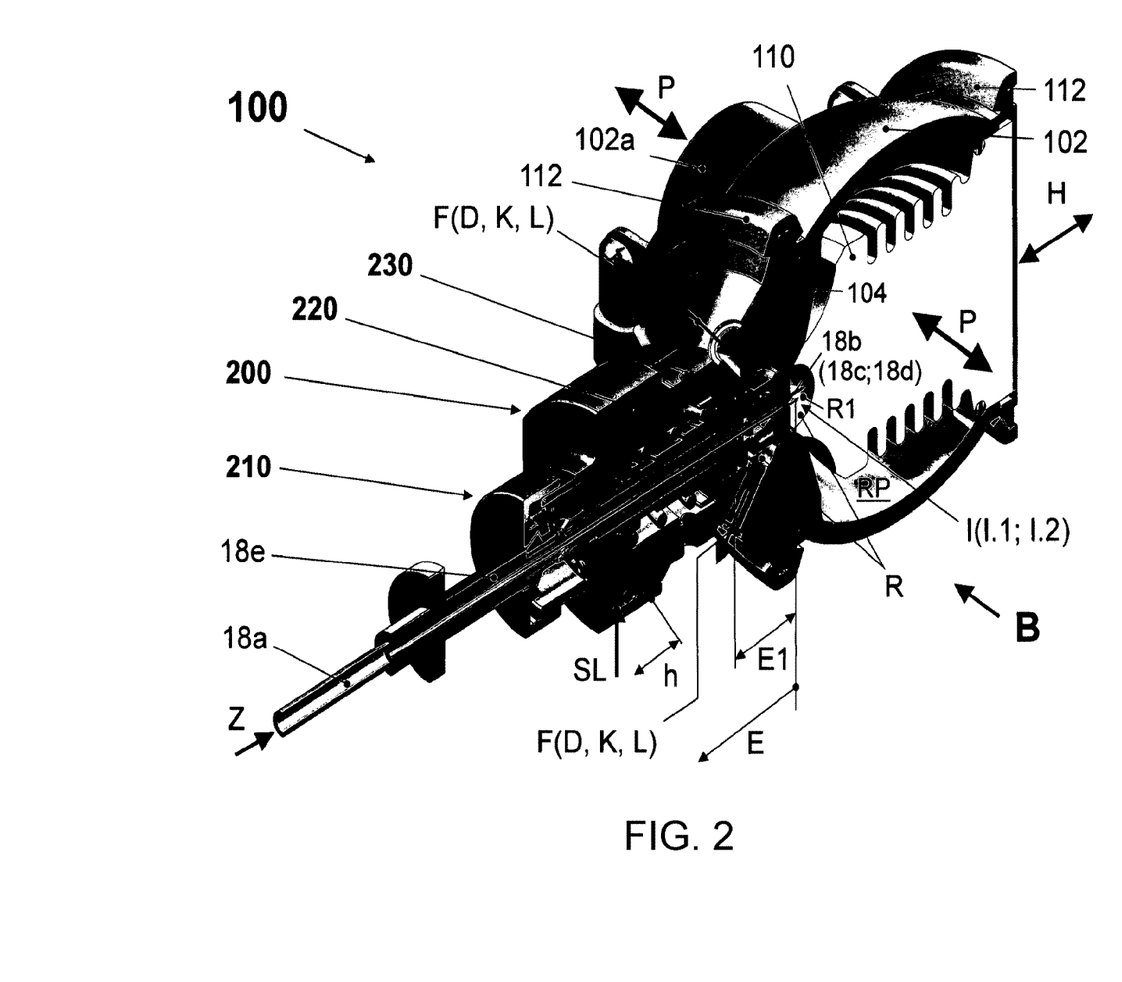
FIG. 2 in a perspective representation, a metering valve for the metering device according to FIG. 1 cut open in its meridian plane; wherein the meridian plane is oriented perpendicular to the flow direction of the aseptic base product flowing in a product conduit section, into which an aseptic additive is delivered in a measured manner, and the metering valve is in its standby position.

The metering position I is provided within the metering valve 100 (FIG. 1), wherein the metering valve 100 forms a product chamber RP, into which the product conduit section 12 opens and from which it exits, an initial chamber E and the terminal part E1 (FIGS. 2, 1).

That part of the initial chamber R remaining after division of the partial chamber R1 has an infeed and a discharge channel 104*a*, 104*b* (FIG. 2), which are optionally blockable respectively via the associated stop valve 26, 28 and wherein the infeed channel 104*aa* can be connected at least with the fourth means 24 for providing sterile steam D. The infeed channel 104*a* can be optionally connected with the fifth means 24*a* for providing sterile condensate K and/or the sixth means 24*b* for providing sterile air L. The temperature sensor 38 is arranged in the discharge channel 104*b* or downstream directly subsequent to the discharge channel 104*b*.

The metering valve 100 is described below in FIGS. 2 to 6 as an example in one embodiment, in which the end section E of the removal conduit 18*a* can be designed in the form of an injection needle 18*b*. The storage container 18 for the additive Z designed as a ductile bag can thus be used unrestrictedly in the metering valve 100 according to the invention in connection with the injection needle 18*b*, which have been known and used in the state of art for quite some time, without requiring any sort of change or modification in terms of the bag 18 and injection needle 18*b*.

Figure 3:
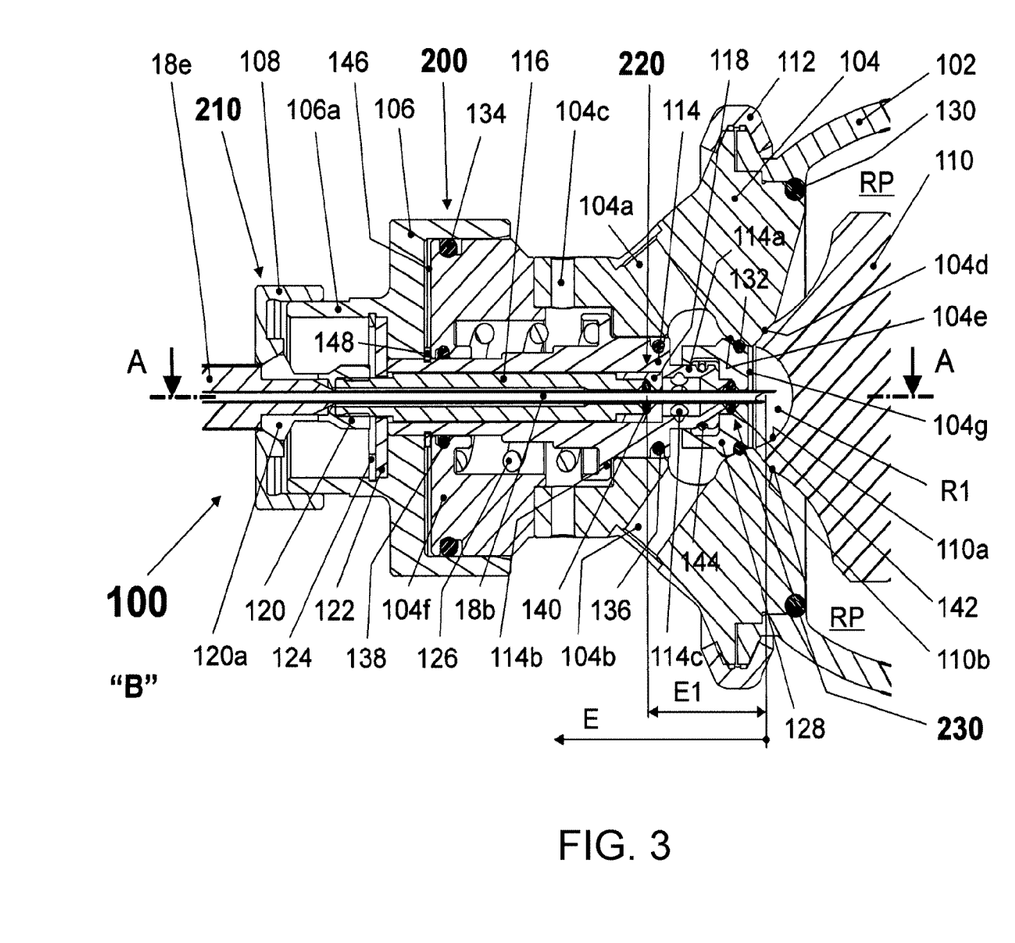
FIG. 3 in a sectional representation, the metering valve cut open in the meridian plane according to FIG. 2 in a viewing direction labeled there with "B"
Figure 4:
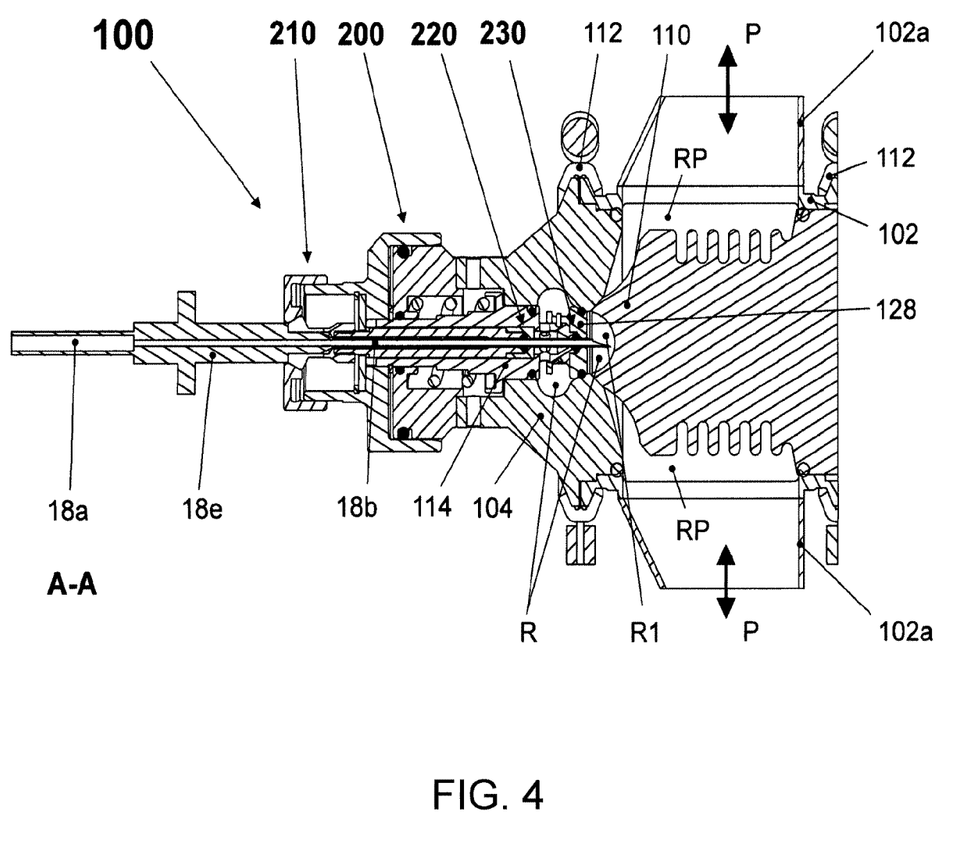
FIG. 4 in a sectional representation, the metering valve according to FIG. 2 in another meridian plane, wherein the associated cut progression in FIG. 3 is labeled with A-A.

The metering valve 100 has the product chamber RP bordered by a valve housing 102, wherein the product conduit section 12 enters and exits the valve housing 102 via two tube sockets 102*a* integrally shaped on the valve housing 102, which are preferably arranged opposite each other (FIGS. 2, 4). Preferably perpendicular to the axis of the tube sockets 102*a*, the valve housing 102 has an unreferenced opening, which is tightly sealed by a housing closure body 104 by means of a housing seal 130. The housing closure body 104 has a passage opening 104*g* to the product chamber RP (FIG. 3). A first sleeve 113, which is arranged coaxially to the passage opening 104*g* and engages in the housing closure body 104 sealed off from outside in a displaceable manner via a first and a second sleeve seal 136, 138, is driven by means of a pressurized spring piston drive 200 and thus executes a second lifting movement h. The end section of the housing closure body 104 facing away from the valve housing 102 is thereby designed as a drive piston 104*f* of the spring piston drive 200 and is penetrated in a displaceable and sealed manner by the first sleeve 114. An associated drive housing 106 is designed in a pot-like manner, forms a drive chamber 146 that can be supplied with a pressurizing agent, preferably control air SL (FIG. 2), with the drive piston 104*f* carrying a second piston seal 134 on the outside and is penetrated by the first sleeve 114 and connected with it in a form- and force-fitting manner. A drive spring 126 of the spring piston drive 200 is supported on one side on the drive piston 104*f* and on the other side on a valve spring retainer 114*b* designed on the first sleeve 114 in such a manner that the reset force of the drive spring 126 pushes the first sleeve 114 in the direction of the passage opening 104*g*. A chamber defining the drive spring 126 is connected with the area surrounding the metering valve 100 via at least one lantern hole 104*c*.

The drive housing 106 transitions into a pot-like clamping housing 106a of a clamping and pressing device 210 delimited by a cap nut 108 on its side facing away from the drive piston 104f, wherein the cap nut 108 acts on a collet 120a penetrated by the end section E via conical effective surfaces such that the end section E, which in the present case is designed as a shaft 18e of the injection needle 18b, through which and in relation to which the collet 120a is axially and radially fixed. The collet 120a ends on the other side in a connection part 120, which is connected with a second sleeve 116 arranged in the first sleeve 114.

The first sleeve 114 is fastened in the bottom of the drive housing 106 between a disc 122, which rests on the bottom on one side and is fixed by a first retaining ring 124 fixed in the clamp housing 106a, and a third retaining ring 148 being received in the first sleeve 114. The second sleeve 116 is supported on its end facing away from the connection part 120 on a pressing sleeve 118 also arranged in the first sleeve 114, which together form a first sealing device 220. The first sealing device 220 is completely penetrated by the end section E and it seals together with the clamping and pressing device 210 the terminal part E1 of the end section E in relation to the first sleeve 114 directly or, as in the present case, indirectly by an axially and radially pressed first sealing means 140. The axial force necessary for this pressing is originally generated by the cap nut 108 and is transmitted to the second sleeve 116 via the collet 120a.

A spool 110 engages in it from the side of the valve housing 102 facing away from the passage opening 104g and is in abutment with a spool seating 110b after a first lifting movement H in its one end position, the closed position, in the circumferential area of the passage opening 104g, which is designed as the first seating 104d. An actuation rod of the spool 110 and its penetration point through the valve housing 102 are not shown. The spool 110 and the penetration point are bridged in a surface-connected way by an unreferenced bellows, preferably a corrugated bellows or corrugated tube. The valve housing 102 is connected on one side with the housing closure body 104 and on the other side with a closure part (not shown), which forms the penetration point and the clamping of the bellows, respectively via a clamp ring connection 112.

In the front side of the spool 110 facing the passage opening 104g, a chamber-forming spool recess 110a is provided (FIG. 3), which forms the initial chamber R together with a chamber located in the housing closure body 104 between the passage opening 104g and the front-side, displaceable end of the sleeve 114, wherein the chamber located in the housing closure body 104 is connected respectively with the area surrounding the metering valve 100 via the intake and the discharge channel 104a, 104b for the fluid F, which can be sterile steam D, sterile condensate K or sterile air L (FIG. 2).

The metering valve 100 also has a closure piston 128, which is penetrated by the terminal part E1 of the end section E and is arranged preferably in a slightly restricted displaceable manner axially and radially on a bearing journal 114a protruding into the initial chamber R arranged on the terminal side of the first sleeve 114. The closure piston 128 is preferably in sealing abutment with a first piston seal 132 in its end position, its closed position, generated by the reset force of the drive spring 126 after the second lifting movement h, in the circumferential area of the passage opening 104g, which is designed as the second seating 104e. In this closed position, the closure piston 128 between itself and the spool recess 110a divides the partial chamber R1 from the initial chamber R and the closure piston 128 is sealed off from the terminal part E1 by an axially and radially pressed second sealing means 142 within the framework of a second sealing device 230. In another end position of the closure piston 128, its open position, generated by a second lifting movement h, the second sealing means 142 is released from the terminal part E1 by a gap's width through its inherent elasticity and all surfaces and areas of the initial chamber R are accessible to be supplied with the fluid F.

The pressing and the broadening of the second sealing means 142 are preferably achieved in that the closure piston 128 and the bearing journal 114a engaging in it form a wedge-shaped annular space surrounding the terminal part E1, which tapers from inside to outside and receives the second sealing means 142. In the closed position of the closure piston 128, the flanks of the wedge-shaped annular space converge far enough that the second sealing means 142 is pressed axially and radially and is thus sealed against the terminal part E1. In the open position of the closure piston 128, the flanks of the wedge-shaped annular space are removed from each other far enough that the second sealing means 142 broadens and is spaced apart from the terminal part E1 by a gap's width under the effect of its inherent elasticity. In this broadened state of the second sealing means 142, it is flushable on all sides with fluid F, because the bearing journal 114a is preferably designed hollow on one side up to the second sealing means 142 and, on the other side, this hollow space is connection in a fluid-accessible manner with the area surrounding the bearing journal 114 and the closure piston 128, the initial chamber R, via at least one channel 114c. The closure piston 128 is pushed preferably with slight radial play onto the bearing journal 114a and is fixed there axially via a second retaining ring 114. This bearing is also designed in a fluid-penetrable manner via suitable unreferenced passages in the shaft of the closure piston 128 (for this, also see FIG. 5).

Figure 5:
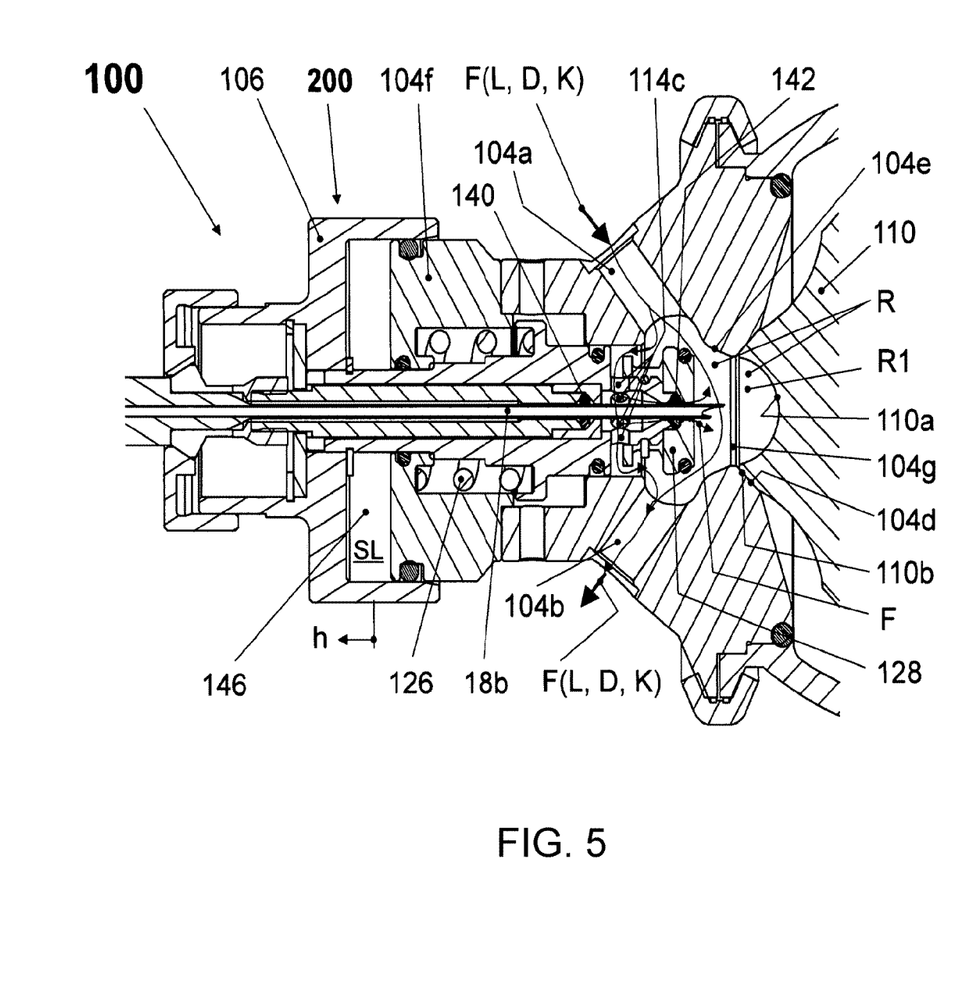
FIG. 5 the sectional representation of the metering valve according to FIG. 3, wherein it is now in its sterilization position and FIG. 6 the sectional representation of the metering valve according to FIG. 3, wherein it is now in its metering position.
Figure 6:
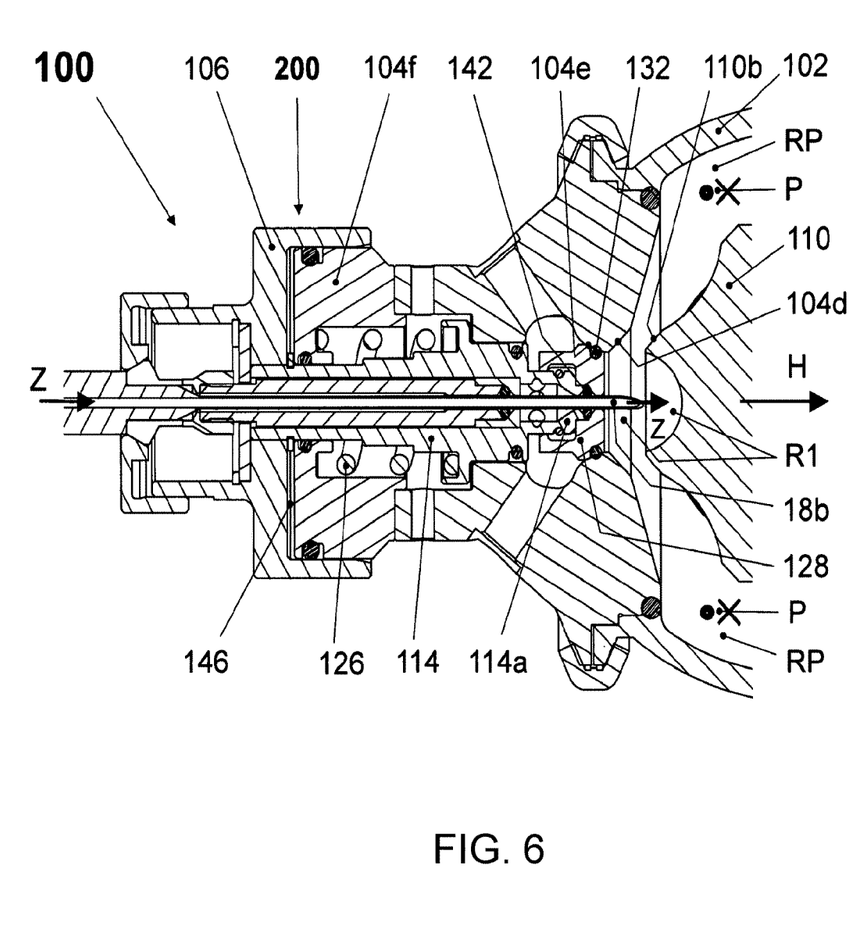

The structure of the metering valve 100 was described above based on FIGS. 2 to 4, in which it is in the so-called standby position, and on FIG. 5, in which it is in the sterilization position. FIG. 1 shows the embedding of the metering valve 100 into the metering device 10. In the standby position according to FIGS. 2 to 4, the drive chamber 146 is not supplied with pressurizing agent, the control air SL (FIG. 2). The closure piston 128 is pressed into its sealing closed position onto the second seating 104e under the influence of the reset force of the drive spring 126. The first and the second sealing means 140, 142 seal the injection needle 18b in the aforementioned manner. The partial chamber R1 formed substantially by the chamber-forming spool recess 110b is divided from the initial chamber R (FIG. 2) by means of the closure piston 128 (also see FIGS. 3 and 4). There is not yet a fluid-accessible connection between the partial chamber R1 and the product chamber RP bordered by the valve housing 102 because the spool 110 with its spool seating 110b is still in its closed position on the associated first seating 104d.

In the sterilization position according to FIG. 5, the closure piston 128 is pushed into its open position through the supply of drive chamber 146 with control air SL. The first sealing means 140 remains pressed and the second sealing means 142 is radially broadened so that the terminal part E1 on the first sealing means 140 remains permanently positioned and sealed and engages in the initial chamber R in a manner that is freely flushable by any fluid F. Fluid F, sterile steam D for sterilization, sterile air L for cooling, sterile condensate K for flushing or sterile air L for blowing out can be supplied via the infeed channel 104a.

In the open position of the closure piston 128, a CIP cleaning (cleaning in place) of all relevant areas of the metering valve 100 can be performed when the spool 110 is also transitioned into its open position around the first lifting movement H, after performing an aseptic measured delivery, when the product conduit section 12 is normally methodically subjected to a chemical cleaning, a CIP cleaning, by means of acid and/or lye and flushing water, wherein the respective cleaning agent is respectively discharge to and via the discharge channel 104*b* via the product conduit section 12.

After the sterilization, the cooling and, if applicable, the flushing with the subsequent blowing out according to FIG. 5, the closure piston 128 is first returned to its closed position, the standby position according to FIGS. 2 to 4, after discontinuation of the control air SL under the reset force of the drive spring 126. Thereupon, the spool 110 can be transitioned into its open position around the first lifting movement H and the partial chamber R1 can be opened towards the product chamber RP, in which the base product P flow. The metering valve 100 is now in the measured delivery position according to FIG. 6, in which the additive Z is delivered in a measured manner to the flowing base product flow-proportionally to the quantity via the discharge opening of the terminal part E1 of the end section E, in this case the injection needle 18*b*.

Instead of the injection needle 18*b*, a hard or a ductilely deformable tube with a smooth end 18*c* can be used in an analogous manner. The terminal part E1 (FIG. 3) of the end section E can also be designed separately from the latter and with a controllable discharge opening. This would then be for example a controllable small metering valve. The optional coupling of this small metering valve to the end section E can then take place for example in turn via an injection needle 18*b*, a hard or ductilely deformable tube with a smooth end 18*c* or an adapter 18*d* for establishing a fluid-accessible connection, wherein the remaining procedural solution characteristics according to the invention are to be transferred to these conditions in an analogous manner.

In order to also achieve in an adequate manner the security, which is achieved by the suggested method for aseptic measured delivery in the area of the metering valve 100, in the area of a storage container 18 designed as a bag and its connection with the removal conduit 18*a*, it is suggested that the bag 18 and at least the removal conduit 18*a* in the delivery state form a sterile unit and are used in this embodiment in the dosing device 10 (FIG. 1). The main characteristics of this unit, its pre- and post-treatment are described briefly below. The bag 18, which preferably has a capacity of for example 5 or 10 liters, for the sterile storage of liquid, aseptic additives Z, such as enzymes, flavors, colorings, lipids, probiotic bacteria and other foodstuffs is, in its unfilled state, a planar, rectangular structure consisting of a suitable plastic, as is used in its basic form in medical technology. As the initial form, a tubular film with suitable diameter is used as a rule, which is assembled onto a first required axial length and is then closed through welding on both open ends, wherein the respective application-specific precautions, uniquenesses or requirements are carried out on or in these ends. It is preferably made of semi-transparent ethylene-vinyl acetate (EVA) with light protection.

In a connection to the removal arrangement containing at least the removal conduit 18*a*, which is preferably executed as a hose fitting, a so-called pressure-control valve is arranged accessible on the hosing fitting from the outside, with which a fluid-accessible connection between the inner space of the bag 18 and the removal arrangement is established through irreversible breaking of a barrier at a predetermined breaking point.

The removal arrangement consists of the removal conduit 18*a* already described above, preferably a removal hose, which is connected with the aforementioned connection in a permanent and sealed manner via a coupling. This can hereby be a form- and/or force-fitting or even a material connection. It opens into the described injection needle 18*b* at the end of the removal conduit 18*a* facing away from the coupling, with which the additive Z is delivered in a measured manner under aseptic conditions into the base product P flowing in the product conduit section 12. Seen in the flow direction of the additive Z, the removal arrangement preferably has a check valve upstream of the injection needle 18*b* and upstream of this a filter. The barrier of the pressure-control valve is first broken after suspension of the bag 18 via a preferred three-point suspension into the metering device 10 and shortly before the start of the aseptic measured delivery at the predetermined breaking point. The bag 18 and the removal arrangement permanently connected with it and fixed on it are sterilized as a cohesive unit with a suitable means. This already occurs before the filling of the bag 18 with the additive Z.

The aforementioned pressure-control valve has a constriction point and it functions as a predetermined breaking point. Sufficient bending torque transversally to the longitudinal axis of the pressure-control valve leads to a complete break of the pressure-control valve at this point so that the pressure-control valve is separated into two parts. The pressure-control valve is, with the free end of the first part first, inserted into the connection and is shifted there axially far enough that, after breaking the pressure-control valve at the predetermined breaking point, the separated first part with the smaller diameter arrives in the bag 18 so that an unrestricted access to the removal arrangement from the inner space of the bag 18 is ensured via an inner passage only opened by the break in the second part.

A method for filling the bag 18 with the liquid additive Z, for storing the additive Z in the bag 18 and for removing the additive Z from the bag 18, respectively under aseptic conditions and performed with a bag 18, as was described above, is performed in the steps listed below:

- An overwrap bag is completely hermetically sealed by welding its still open side around the bag 18.
- The overwrapped bag 18 is delivered to the metering device 10, there it is removed from the overwrap bag and positioned in its suspended position in the metering device 10 via the three-point suspension (FIG. 1). In order to protect it from damage during transport, the overwrap bag can in turn be received in a transport packaging, for example in a box.
- The injection needle 18*b* on the end of the removal arrangement is received in the metering valve 100 according to FIGS. 2 to 6 and the associated aforementioned description.
- In terms of timing, a fluid-accessible connection is established between the inner space of the bag 18 and the removal arrangement by breaking the barrier at the predetermined breaking point in the pressure-control valve shortly before the measured delivery of the liquid additive Z into the base product P flowing in the product conduit section 12.
- The liquid additive Z is fed in a forced manner and flow-proportional to the flowing base product P, controlled by the control device 50, from the bag 18 to the discharge point of the injection needle 18*b* through third means 22 acting on the removal conduit 18*b* from outside.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A metering device (10; 10.1, 10.2), with a product conduit section (12), through which a base product (P) forcibly flows, with at least one storage container (18; 18.1, 18.2) for an additive (Z), which is connected with an associated metering point (I; I.1, I.2) respectively via a removal conduit (18*a*), which is arranged on or respectively in the product conduit section (12), with third means (22) for forcibly conveying the additive (Z), with first and second means (14, 20) for the quantity-based capturing of the base product (P) and of the additive (Z), with fourth means (24) for providing sterile steam (D) and with a control device (50) assigned to the metering device (10; 10.1, 10.2), wherein
the metering point (I; I.1, I.2) is provided within a metering valve (100), which forms a product chamber (PR), into which the product conduit section (12) opens and from which it exits, an initial chamber (R) and a partial chamber (R1) as well as a receiver of an end section (E) and of a terminal side (E1).

2. The metering device according to claim 1, wherein:
that part of the initial chamber (R) remaining after division of the partial chamber (R1), has an infeed and a discharge channel (104*a*, 104*b*), which are optionally blockable via an associated stop valve (26, 28) and wherein the infeed channel (104*a*) can be connected at least with the fourth means (24) for providing sterile steam (D).

3. The metering device according to claim 2, wherein:
the infeed channel (104*a*) can be optionally connected with a fifth means (24*a*) for providing sterile condensate (K) and/or a sixth means (24*b*) for providing sterile air (L).

4. The metering device according to claim 2, wherein:
a temperature sensor (38) is arranged immediately following the discharge channel (104*b*) in the discharge channel (104*b*) or downstream.

5. The metering device according to claim 1, wherein:
the storage container (18) and at least the removal conduit (18*a*) form a sterile unit in the delivery state.

6. The metering device according to claim 1, wherein:
the end section (E) with its integral terminal part (E1) is designed as one piece as an injection needle (18*b*) or a tube with a smooth end (18*c*).

7. The metering device according to claim 1, wherein:
the terminal part (E1) is designed separately from the end section (E) and with a controllable discharge opening, that the end section (E) is designed as an injection needle (18*b*) or a tube with a smooth end (18*c*) or as an adapter (18*d*) for establishing a fluid-accessible connection with the terminal part (E1) and that the end section (E) is connected in a fluid-accessible manner with the terminal part (E1).

8. The metering device according to claim 1, wherein:
the storage container (18) is designed in the form of a flexible bag and that the bag (18) filled with the additive (Z) and at least the removal conduit (18*a*) are sealed in a PE overwrap and subjected to gamma irradiation for the purpose of external sterilization.

9. A metering valve (100) for a metering device (10) according to claim 1, wherein:
a valve housing (102) arranged in the product conduit section (12) and bordering the product chamber (RP),
a housing closure body (104) closing the valve housing (102) on one side with a passage opening (104*g*) to the product chamber (RP),
a first sleeve (114), which is arranged coaxially to the passage opening (104*g*) and engages in the housing closure body (104) in a displaceable and sealed manner from outside and is driven by means of a spring piston drive (200) supplied with pressurizing agent and thus executes a second lifting movement (h),
a clamping and pressing device (210), which is penetrated by the end section (E) and fixes the latter radially and axially,
a first sealing device (220) being received inside the first sleeve (114), which is penetrated by the end section (E) and which together with the clamping and pressing device (210) seals the terminal part (E1) of the end section (E) with respect to the first sleeve (114) directly or indirectly through an axially and radially pressed first sealing means (140),
a spool (110), which engages in it from the side of the valve housing (102) facing away from the passage opening (104*g*), and is in abutment with a spool seating (110*b*) after a first lifting movement (H) in its one end position in the circumferential area of the passage opening (104*g*), which is designed as a first seating (104*d*),
a chamber-forming spool recess (110*a*) provided in the front surface of the spool (110) facing the passage opening (104*g*), which forms the initial chamber (R) together with a chamber located in the housing closure body (104) between the passage opening (104*g*) and the front-side, displaceable end of the first sleeve (114), wherein the chamber located in the housing closure body (104) is connected respectively with the surrounding area of the metering valve (100) via an infeed and a discharge channel (104*a*, 104*b*),
a closure piston (128), which is penetrated by the terminal part (E1) of the end section (E) and is arranged on a bearing journal (114*a*) arranged on the end side on the first sleeve (114) and protruding into the initial chamber (R) and is in sealing abutment in its end position, the closed position, generated by a drive spring (126) in the spring piston drive (200) after the second lifting movement (h), in the circumferential area of the passage opening (104*g*), which is designed as the second seating (104*e*), wherein the closure piston (128) in its closed position between itself and the spool recess (110*a*) divides the partial chamber (R1) from the initial chamber (R) and the closure piston (128) is sealed off with respect to the terminal part (E1) by an axially and radially pressed second sealing means (142) within the framework of a second sealing device (230) and
another end position of the closure piston (128), the open position, generated with the second lifting movement (h), in which the second sealing means (142) is released from the terminal part (E1) by a gap's width and all surfaces and areas of the initial chamber (R) are accessible for application of a fluid (F), consisting of sterile steam (D) or sterile air (L) or sterile condensate (K).

10. The metering valve according to claim 9, wherein:
the end section of the housing closure body (104) facing away from the valve housing (102) is designed as a drive piston (104*f*) of the spring piston drive (200) and is penetrated in a shiftable and sealed manner by the first sleeve (114), that an assigned drive housing (106) is designed in a pot-like manner and penetrated by the first sleeve (114) and connected with it in a form- and force-fitting manner, and that the drive spring (126) on one side on the drive piston (104*f*) and on the other side on the first sleeve (114) is supported in a manner such that the reset force of the drive spring (126) transfers the closure piston (128) into its closed position.

11. The metering valve according to claim 10, wherein:

the drive housing (106) on its side facing away from the drive piston (104*f*) transitions into a pot-like clamp housing (106*a*) of the clamping and pressing device (210) delimited by a cap nut (108) and that the cap nut (108) acts via conical effective areas on a collet (120*a*) penetrated by the end section (E) such that the end section (E) is determined axially and radially by the collet (120*a*).

12. The metering valve according to claim 11, wherein:

the collet (120*a*) is connected with the one end of a second sleeve (116) received in the first sleeve (114) and completely penetrated by the end section (E) and acts axially on the latter such that it presses the first sealing means (140) axially and radially with its other end.

13. The metering valve according to claim 9, wherein:

the closure piston (128) and the bearing journal (114*a*) engaging in it form a wedge-shaped annular space surrounding the terminal part (E1), which tapers from inside to outside and receives the second sealing means (142), that in the closed position of the closure piston (128) the flanks of the wedge-shaped annular space converge far enough that the second sealing means (142) is pressed axially and radially and is thus sealed against the terminal part (E1) and that in the open position of the closure piston (128) the flanks of the wedge-shaped annular space are spaced apart from each other far enough that the second sealing means (142) broadens and is spaced apart from the terminal part (E1) by a gap's width.

* * * * *